United States Patent
Arabshahi et al.

(10) Patent No.: US 12,042,357 B2
(45) Date of Patent: Jul. 23, 2024

(54) BELLOWS BANDAGE DRUG DELIVERY SYSTEM

(71) Applicants: Azadeh Arabshahi, Sherwood, OR (US); Hamid Arabshahi, Sherwood, OR (US)

(72) Inventors: Azadeh Arabshahi, Sherwood, OR (US); Hamid Arabshahi, Sherwood, OR (US)

( * ) Notice: Subject to any disclaimer, the term of this patent is extended or adjusted under 35 U.S.C. 154(b) by 173 days.

(21) Appl. No.: 17/691,897

(22) Filed: Mar. 10, 2022

(65) Prior Publication Data
US 2023/0285196 A1  Sep. 14, 2023

(51) Int. Cl.
| | | |
|---|---|---|
| A61F 13/00 | (2024.01) | |
| A61F 13/02 | (2024.01) | |
| A61K 9/00 | (2006.01) | |
| A61L 15/44 | (2006.01) | |

(52) U.S. Cl.
CPC ........ *A61F 13/00063* (2013.01); *A61F 13/02* (2013.01); *A61K 9/0014* (2013.01); *A61L 15/44* (2013.01)

(58) Field of Classification Search
None
See application file for complete search history.

(56) References Cited

U.S. PATENT DOCUMENTS

2015/0342900 A1* 12/2015 Putnins ................ A61K 9/7084
604/290

FOREIGN PATENT DOCUMENTS

WO    WO 2012/171920    * 12/2012

* cited by examiner

*Primary Examiner* — Patricia Duffy
*Assistant Examiner* — Garen Gotfredson
(74) *Attorney, Agent, or Firm* — Lyman Moulton, Esq.; Moulton Patents PLLC

(57) ABSTRACT

Medaide is the only product of its kind that provides a band-aid strategically developed with a medicine carrier reservoir that can be easily puncture to release medication onto an affected skin site. This unprecedented product is uniquely designed with a durable adhesive skin color semi-transparent band-aid to complement diverse users and comes individually packed for easy transport and to preserve the sanitization of each covering.

6 Claims, 3 Drawing Sheets

BELLOWS BANDAGE DRUG DELIVERY SYSTEM

BACKGROUND

Treating abrasions, disorders, or symptoms on the surface of the skin, such as: a bite, cut, burn, acne, etc., while on-the-go can be a challenge especially when medication is required. Often when an individual has to address a wound via an ointment and a band-aid covering the process is tedious as the ointment tends to spread thereby causing the band-aid to lose its adhesiveness. There have been no products available as original equipment or as an aftermarket to address this problem.

An apparatus or system to help treat wounds in a fast, simple and efficient manner, while on the go is not being met by any known device or system at present. There have been no products available as original equipment or as an aftermarket to address this problem either.

SUMMARY OF THE INVENTION

The main purpose of the bellows bandage drug delivery system is to provide users with a pre-medicated band-aid with a pressure sensitive reservoir that releases specific medications upon activation of a bellows by skin movement and muscle movement and pressure to relieve and calm itching and inflammation associated with varying skin ailments.

Figure 1:
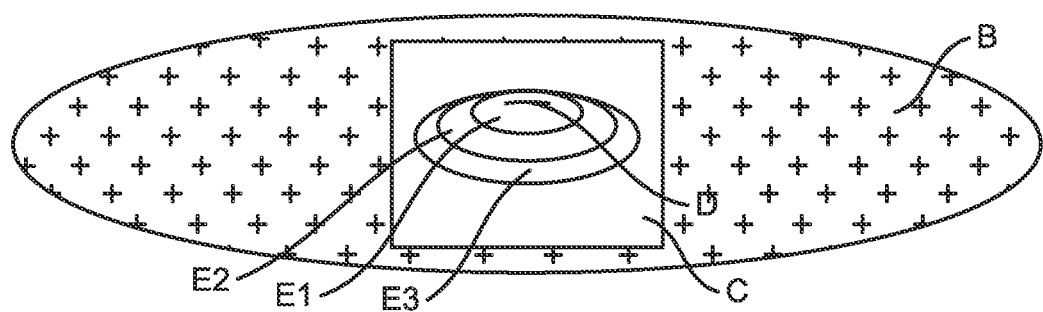
FIG. 1 is a top perspective view of the bellows bandage drug delivery system in accordance with an embodiment of the present disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one Skilled in the relevant art and having possession of this disclosure, are to be considered within the scope of the invention.

Figure 2:
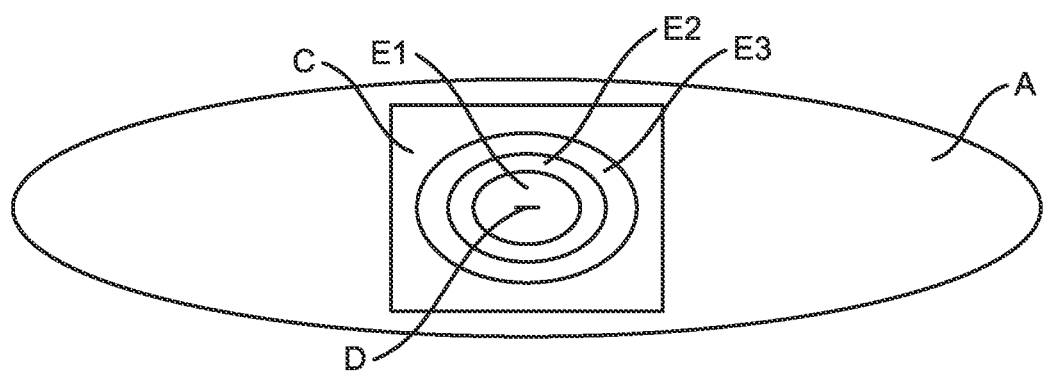
FIG. 2 is a top elevational view of the bellows bandage drug delivery system in accordance with an embodiment of the present disclosure.
Figure 3:
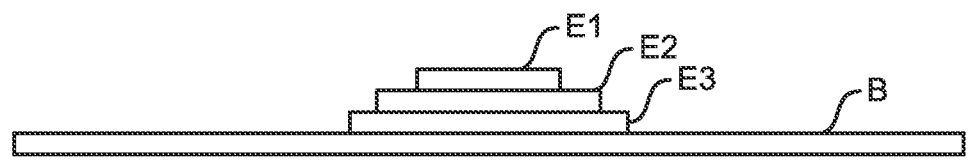
FIG. 3 is a side elevational view of the bellows bandage drug delivery system in accordance with an embodiment of the present disclosure.

FIG. 1 is a top perspective view of the bandage drug delivery system showing: peel-off cover referenced as A, adhesive skin color semi-transparent Band-Aid with thin protective shield referenced as B, non-adhesive pad of Band-Aid referenced as C, 2 mm slit to release medication when pressed referenced as D, medication chamber with bellows folds when pressed down to release referenced as E1, E2 and E3, in accordance with an embodiment of the present disclosure. FIG. 2 is a top elevational view of the bandage drug delivery system in accordance with an embodiment of the disclosure. Reference letters are same for same limitations as described for FIG. 1 above including bellows folds E1, E2 and E3. FIG. 3 is a side view of the bandage drug delivery system in accordance with an embodiment of the disclosure. Reference letters are same for same limitations as described in FIG. 1 above including bellows folds E1, E2 and E3.

The present disclosed bandage drug delivery system, also known as "Medaide" offers a modem first-aid option that covers damaged skin areas with a protective bandage that also simultaneously releases medication to treat the affected area, allowing for a less messy and more efficient means to addressing and expediting recovery. Expanding on the initial design of an average band-aid, Medaide introduces a novel bandage that carries a prescribed medication within its bellows structure to meet the care for a particular issue. To use, for example to treat an insect bite, one would simply apply the Medaide option best suited with medication to relieve the poison on a targeted skin area, and then slightly depress the breakable slit D and depress or activate the bellows membranes of the medication chamber E1, E2 and E3. The special reservoir instantly releases the medication directly to the site of the wounded are to calm itching and inflammation. To further enhance functionality, the strategically placed bellows chamber can be manufacture to carry various types of medicine for different types of situations, such as acne, burn, cuts, dermatitis, eczema, and so forth. This innovative, top-quality, product ensures a fully operational band-aid that combines the functions of both medicine and a protective shield which allows convenience of application when individuals are on-the-go and provides instant relief from discomfort Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

What is claimed is:

1. A bandage drug delivery system comprising:
   a substrate configured to have an underside and to be air permeable and flexible with a skin movement and to shield a wound adjacent the underside; and
   a bellows disposed on the underside and comprising a medication and defining a slit in a top of the bellows opposite a bottom adjacent the underside,
   wherein the slit is scored and configured to open upon an applied pressure thereto and the bellows is configured to pump the medication from the underside through the open slit, and
   wherein the bellows comprises multiple fold levels from a broadest fold level adjacent the underside to a narrowest fold level at the top of the bellows and an intermediate fold level between the broadest and the narrowest fold levels.

2. The bandage drug delivery system of claim 1, further comprising one or more medications to treat burn, cuts, dermatitis, eczema, and/or bacterial infection.

3. The bandage drug delivery system of claim 1, wherein the slit comprises a length of 2 mm.

4. The bandage drug delivery system of claim 1, wherein the substrate underside further comprises an adhesive.

5. The bandage drug delivery system of claim 4 further comprising a peel off cover for the adhesive.

6. The bandage drug delivery system of claim 1, wherein the bellows further comprises a medication chamber with a breakable membrane configured to release the medication in response to a pressure applied thereto.

\* \* \* \* \*